US008308892B2

(12) United States Patent
Dershem

(10) Patent No.: US 8,308,892 B2
(45) Date of Patent: Nov. 13, 2012

(54) DI-CINNAMYL COMPOUNDS AND METHODS FOR USE THEREOF

(75) Inventor: Stephen M Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 668 days.

(21) Appl. No.: 12/421,616

(22) Filed: Apr. 9, 2009

(65) Prior Publication Data

US 2009/0288768 A1 Nov. 26, 2009

Related U.S. Application Data

(60) Provisional application No. 61/043,716, filed on Apr. 9, 2008.

(51) Int. Cl.
*B41J 2/16* (2006.01)
*C07C 237/00* (2006.01)
*C07C 61/12* (2006.01)
*C07F 7/10* (2006.01)
*C07F 7/00* (2006.01)
*C09J 1/00* (2006.01)
*C09J 4/00* (2006.01)

(52) U.S. Cl. ........ 156/326; 564/155; 562/500; 556/419; 556/450; 524/104; 106/287.11; 106/287.13; 106/287.2

(58) Field of Classification Search .................. 156/326; 524/104; 106/287.11, 287.13, 287.2, 287.22
See application file for complete search history.

(56) References Cited

U.S. PATENT DOCUMENTS

| | | |
|---|---|---|
| 4,111,879 A | 9/1978 | Mori et al. |
| 4,968,738 A | 11/1990 | Dershem |
| 5,045,127 A | 9/1991 | Dershem et al. |
| 5,064,480 A | 11/1991 | Dershem et al. |
| 5,232,962 A | 8/1993 | Dershem et al. |
| 5,306,333 A | 4/1994 | Dershem et al. |
| 5,358,992 A | 10/1994 | Dershem et al. |
| 5,403,389 A | 4/1995 | Dershem |
| 5,447,988 A | 9/1995 | Dershem et al. |
| 5,489,641 A | 2/1996 | Dershem |
| 5,602,205 A | 2/1997 | Singh et al. |
| 5,646,241 A | 7/1997 | Dershem et al. |
| 5,714,086 A | 2/1998 | Osuna et al. |
| 5,717,034 A | 2/1998 | Dershem et al. |
| 5,718,941 A | 2/1998 | Dershem et al. |
| 5,753,748 A | 5/1998 | Dershem et al. |
| 5,760,165 A | 6/1998 | Dao et al. |
| 5,861,111 A | 1/1999 | Dershem et al. |
| 5,969,036 A | 10/1999 | Dershem |
| 5,973,166 A | 10/1999 | Mizori et al. |
| 6,034,150 A | 3/2000 | Hoyle et al. |
| 6,034,194 A | 3/2000 | Dershem |
| 6,034,195 A | 3/2000 | Dershem |
| 6,121,358 A | 9/2000 | Dershem et al. |
| 6,187,886 B1 | 2/2001 | Husson et al. |
| 6,211,320 B1 | 4/2001 | Dershem et al. |
| 6,265,530 B1 | 7/2001 | Herr et al. |
| 6,281,314 B1 | 8/2001 | Tong |
| 6,300,456 B1 | 10/2001 | Musa |
| 6,316,566 B1 | 11/2001 | Ma et al. |
| 6,355,750 B1 | 3/2002 | Herr |
| 6,369,124 B1 | 4/2002 | Hoyle et al. |
| 6,423,780 B1 | 7/2002 | Dershem et al. |
| 6,429,281 B1 | 8/2002 | Dershem et al. |
| 6,521,731 B2 | 2/2003 | Dershem et al. |
| 6,620,946 B2 | 9/2003 | Dershem et al. |
| 6,699,929 B2 | 3/2004 | Musa et al. |
| 6,743,852 B2 | 6/2004 | Dershem et al. |
| 6,750,301 B1 | 6/2004 | Bonneau et al. |
| 6,790,597 B2 | 9/2004 | Dershem |
| 6,825,245 B2 | 11/2004 | Dershem |
| 6,831,132 B2 | 12/2004 | Liu et al. |
| 6,852,814 B2 | 2/2005 | Dershem et al. |
| 6,855,745 B2 | 2/2005 | Hoyle et al. |
| 6,908,957 B2 | 6/2005 | Musa et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 7,102,015 B2 | 9/2006 | Dershem et al. |
| 7,157,587 B2 | 1/2007 | Mizori et al. |
| 7,176,044 B2 | 2/2007 | Forray et al. |

(Continued)

FOREIGN PATENT DOCUMENTS

CN 1187507 A 7/1998

(Continued)

OTHER PUBLICATIONS

Andersson et al., "Initiator-Free Photopolymerization of an Aliphatic Vinyl Ether-Maleimide Monomer", *J Coatings Tech 69:* 1997, 91-95.
Grenier-Loustalot et al., "Monofunctional maleimide or acetylene tednnlnated model compounds-I. Molten state homopolymerization reactivity and kinetics", *European Polymer Journal 34:* 1998, 1705-1714.
Kohi et al., "Co-Polymerization of Maleimides and Vinyl Ethers: A Structural Study", *Macromolecules 31:* 1998, 5681-5689.
Yamazaki et al., "Effect of N-substrtuents on polymerization reactivity of N-alkylitaconimides in radical polymerization", *European Polymer Journal 33:* 1997, 157-162.

*Primary Examiner* — Katarzyna Wyrozebski Lee
*Assistant Examiner* — Daniel Lee
(74) *Attorney, Agent, or Firm* — The Law Office of Jane K. Babin, Professional Corporation; Jane K. Babin

(57) ABSTRACT

The invention generally relates to di-cinnamyl compounds useful in a variety of adhesive applications. More specifically, the invention provides chain-extended bismaleimides and methods for generating them by reaction with di-cinnamyl compounds, including particular di-cinnamyl compounds disclosed herein. Invention di-cinnamyl compounds can also be used as co-monomers in a Diels-Alder type cure, and can act as a co-monomer in a thermoset composition with a maleimide monomer.

18 Claims, No Drawings

U.S. PATENT DOCUMENTS

| | | | |
|---|---|---|---|
| 7,199,249 B2 | 4/2007 | Liu et al. | |
| 7,208,566 B2 | 4/2007 | Mizori et al. | |
| 7,285,613 B2 | 10/2007 | Dershem et al. | |
| 7,309,724 B2 | 12/2007 | Dershem et al. | |
| 7,326,754 B2 | 2/2008 | Nikolic et al. | |
| 7,517,925 B2 | 4/2009 | Dershem et al. | |
| 7,678,879 B2 | 3/2010 | Dershem | |
| 2002/0010281 A1 | 1/2002 | Musa et al. | |
| 2002/0062923 A1 | 5/2002 | Forray | |
| 2002/0099168 A1 | 7/2002 | Dershem et al. | |
| 2002/0188137 A1 | 12/2002 | Dershem et al. | |
| 2002/0193541 A1 | 12/2002 | Dershem et al. | |
| 2002/0198356 A1 | 12/2002 | Dershem et al. | |
| 2003/0008992 A1 | 1/2003 | Dershem et al. | |
| 2003/0055121 A1 | 3/2003 | Dershem et al. | |
| 2003/0060531 A1 | 3/2003 | Dershem et al. | |
| 2003/0087999 A1 | 5/2003 | Dershem et al. | |
| 2003/0109666 A1 | 6/2003 | Dershem et al. | |
| 2003/0125551 A1 | 7/2003 | Dershem et al. | |
| 2003/0129438 A1 * | 7/2003 | Becker et al. | 428/620 |
| 2003/0199638 A1 | 10/2003 | Liu et al. | |
| 2003/0208016 A1 | 11/2003 | Dershem et al. | |
| 2004/0006166 A1 | 1/2004 | Liu et al. | |
| 2004/0019224 A1 | 1/2004 | Dershem et al. | |
| 2004/0077798 A1 | 4/2004 | Dershem et al. | |
| 2004/0082724 A1 | 4/2004 | Dershem et al. | |
| 2004/0102566 A1 | 5/2004 | Forray et al. | |
| 2004/0123948 A1 | 7/2004 | Dershem et al. | |
| 2004/0225026 A1 | 11/2004 | Mizori et al. | |
| 2004/0225045 A1 | 11/2004 | Forray | |
| 2004/0225059 A1 | 11/2004 | Mizori et al. | |
| 2005/0107542 A1 | 5/2005 | Liu et al. | |
| 2005/0136620 A1 | 6/2005 | Dershem et al. | |
| 2005/0137277 A1 | 6/2005 | Dershem et al. | |
| 2005/0137340 A1 | 6/2005 | Nikolic et al. | |
| 2005/0267254 A1 | 12/2005 | Mizori et al. | |
| 2005/0272888 A1 | 12/2005 | Dershem et al. | |
| 2006/0009578 A1 | 1/2006 | Dershem | |
| 2006/0030672 A1 | 2/2006 | Nikolic et al. | |
| 2006/0063014 A1 | 3/2006 | Forray | |
| 2006/0069232 A1 | 3/2006 | Dershem | |
| 2006/0116476 A1 | 6/2006 | Cheng | |
| 2006/0142517 A1 | 6/2006 | Dershem | |
| 2007/0060683 A1 | 3/2007 | Musa et al. | |
| 2007/0155869 A1 | 7/2007 | Dershem et al. | |
| 2007/0205399 A1 | 9/2007 | Mizori | |
| 2007/0299154 A1 | 12/2007 | Dershem et al. | |
| 2008/0017308 A1 | 1/2008 | Dershem et al. | |
| 2008/0075961 A1 | 3/2008 | Mizori | |
| 2008/0075963 A1 | 3/2008 | Dershem | |
| 2008/0075965 A1 | 3/2008 | Dershem | |
| 2008/0103240 A1 | 5/2008 | Dershem | |
| 2008/0142158 A1 | 6/2008 | Dershem | |
| 2008/0146738 A1 | 6/2008 | Dershem | |
| 2008/0160315 A1 | 7/2008 | Forray et al. | |
| 2008/0191173 A1 | 8/2008 | Dershem et al. | |
| 2008/0210375 A1 | 9/2008 | Dershem et al. | |
| 2008/0251935 A1 | 10/2008 | Dershem | |
| 2008/0257493 A1 | 10/2008 | Dershem | |
| 2008/0262191 A1 | 10/2008 | Mizori | |
| 2009/0061244 A1 | 3/2009 | Dershem | |
| 2009/0215940 A1 | 8/2009 | Dershem | |
| 2010/0041803 A1 | 2/2010 | Dershem | |
| 2010/0041823 A1 | 2/2010 | Dershem | |
| 2010/0041832 A1 | 2/2010 | Dershem | |
| 2010/0041845 A1 | 2/2010 | Dershem et al. | |
| 2010/0056671 A1 | 3/2010 | Dershem | |
| 2010/0063184 A1 | 3/2010 | Dershem | |

FOREIGN PATENT DOCUMENTS

| | | |
|---|---|---|
| EP | 0393713 | 6/1994 |
| EP | 1156034 | 11/2001 |
| EP | 1156036 | 11/2001 |
| WO | WO2004099331 | 11/2004 |
| WO | WO-2005121190 | 12/2005 |
| WO | WO-2007100329 | 9/2007 |
| WO | WO-2008077141 | 6/2008 |
| WO | WO-2008124797 | 10/2008 |
| WO | WO-2008130894 | 10/2008 |
| WO | WO-2010/019832 | 2/2010 |

* cited by examiner

DI-CINNAMYL COMPOUNDS AND METHODS FOR USE THEREOF

RELATED APPLICATIONS

This application claims the benefit of priority under 35 USC §119 of U.S. Provisional Application Ser. No. 61/043,716 filed Apr. 9, 2008, the entire disclosure of which is incorporated herein by reference.

FIELD OF THE INVENTION

The present invention relates to thermosetting adhesive compositions, methods of preparation and uses therefor. In particular, the present invention relates to thermosetting compositions containing di-cinnamyl compounds.

BACKGROUND OF THE INVENTION

As the electronics industry advances, and production of light weight components increases, the development of new materials gives producers increased options for further improving the performance and ease of manufacture of such components. Adhesive compositions are used for a variety of purposes in the fabrication and assembly of semiconductor packages and microelectronic devices. The more prominent uses include bonding of electronic elements such as integrated circuit (IC) chips to lead frames or other substrates, and bonding IC chips to other IC chips. Adhesives useful for electronic packaging applications typically exhibit properties such as good mechanical strength, curing properties that do not affect the component or the carrier, and rheological properties compatible with application to microelectronic and semiconductor components.

The microelectronics industry continues to require new adhesives that are able to meet its varying demands. Accordingly, there is a need for the development of materials to address the requirements of this rapidly evolving industry.

SUMMARY OF THE INVENTION

The present invention provides di-cinnamyl compounds useful as adhesive monomers and for chain-extending bismaleimides. In certain embodiments, the di-cinnamyl compounds of the invention have the structure of formula I

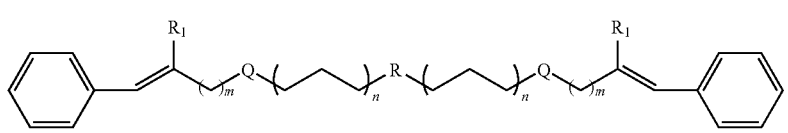

where each Q is independently —C(O)O—, —C(O)NH—, —OC(O)O—, —O—, —OC(O)—, —NHC(O)—, or —OC(O)NH—; R is a substituted or unsubstituted $C_2$ to $C_{100}$ aliphatic, heteroaliphatic, cycloaliphatic, branched aliphatic, branched heteroaliphatic, heterocyclic, heteroaromatic, aryl, polyaryl or a silicone containing 2-20 silicon atoms optionally substituted with one or two methyl or phenyl groups; each $R_1$ is independently H or Me; each m is independently 0 or 1; and each n is independently 0 or 1.

In certain aspects of the invention, R is a $C_2$ to $C_{100}$ cycloaliphatic. In other aspects, R is a $C_2$ to $C_{100}$ branched aliphatic. In yet further aspects, R is a $C_{36}$ branched aliphatic moiety.

In other embodiments of the invention, the di-cinnamyl compounds have the structure of formula II:

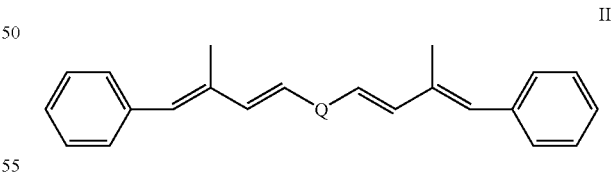

where Q is —C(O)—.

Exemplary di-cinnamyl compound of the invention include, but are not limited to:

Compound 1

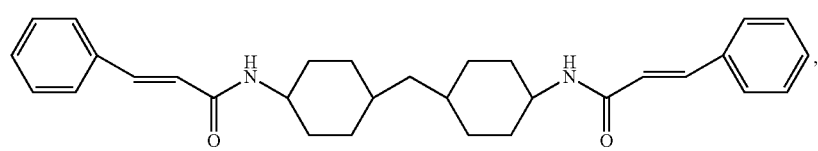

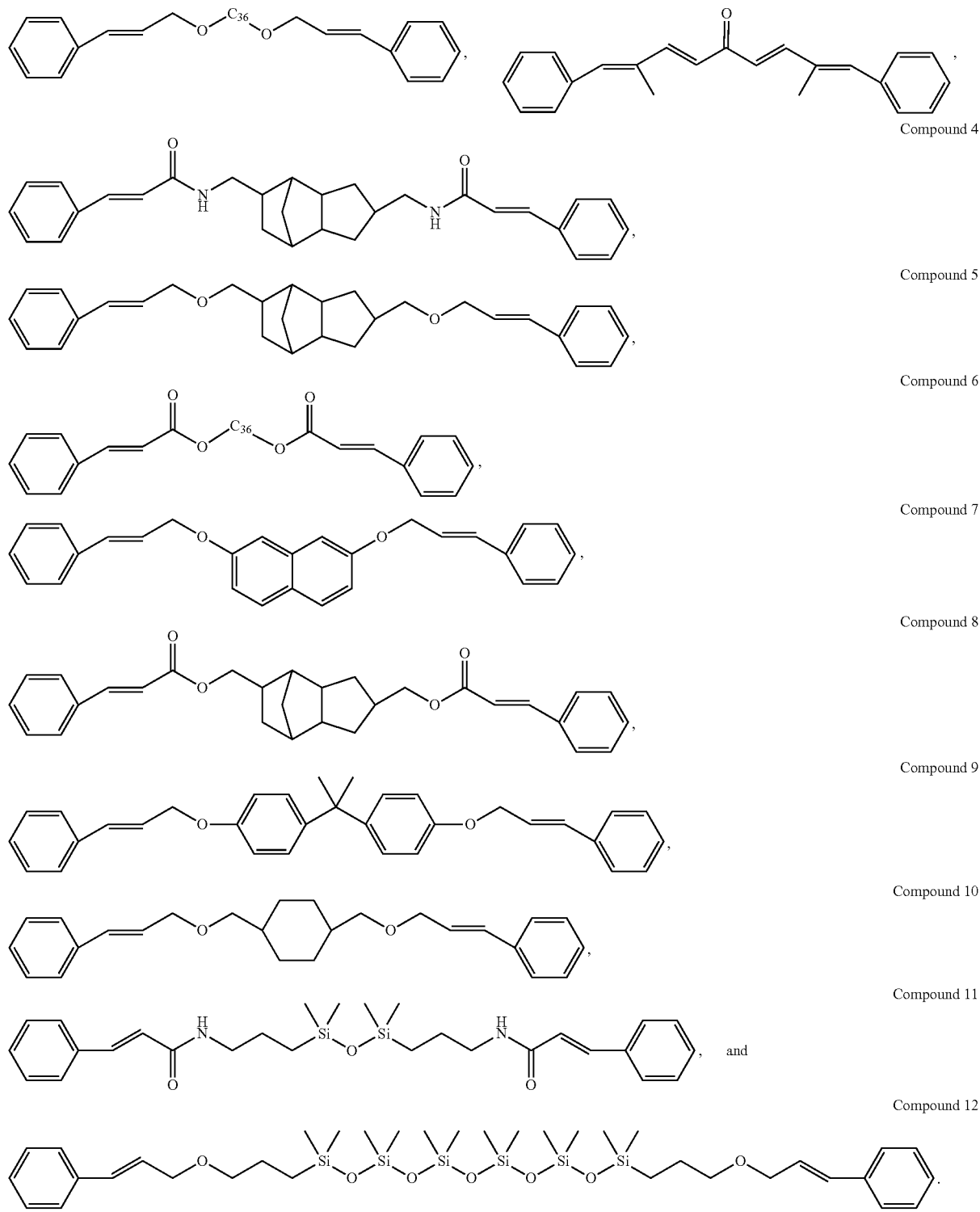

The present invention also provides methods for preparing chain-extended bismaleimides including the steps of: mixing a molar excess of at least one bismaleimide with at least one di-cinnamyl compound, and heating the mixture thereby preparing a chain-extended bismaleimide. Chain extension is conducted at around at least about 100° C., typically about 130° C., and most often at about 150° C. Optimally, the chain extension reaction is conducted in the presence of one or more free radical inhibitors.

The di-cinnamyl compounds used in such methods of the invention can be any di-cinnamyl compounds, but will typically be di-cinnamyl esters, di-cinnamyl amides, di-cinnamyl ethers, di-cinnamyl urethanes, or di-cinnamyl ketones. In certain embodiments, the di-cinnamyl compound will be a compound having the structure set forth herein as formula I or II, such as, without limitation, compounds 1, 2, 3, 4, 5, 6, 7, 8, 9, 10, 11, and 12.

The present invention also provides methods for reducing the brittleness of a cured bismaleimide thermoset that include the steps of mixing a molar excess of at least one bismaleimide with at least one di-cinnamyl compound, thereby producing a bismaleimide thermoset; heating the bismaleimide thermoset mixture, thereby chain-extending the bismaleimide in the bismaleimide thermoset mixture, which also effectively incorporates the di-cinnamyl compound into the thermoset; and curing the chain-extended bismaleimide thermoset, thereby reducing the brittleness of the cured bismaleimide thermoset.

The present invention also provides methods for increasing the adhesion of a cured bismaleimide thermoset including the steps of mixing a molar excess of at least one bismaleimide with at least one di-cinnamyl compound, thereby producing a bismaleimide thermoset mixture; heating the bismaleimide thermoset mixture to chain-extend the bismaleimide in the mixture; and curing the chain-extended bismaleimide thermoset mixture, thereby increasing the adhesion of the cured bismaleimide thermoset. In certain embodiments, the method increases adhesion of the bismaleimide thermoset by at least about 25%.

Also provided by the invention are chain-extended bismaleimides prepared according to the methods of the invention and adhesive compositions that include the chain-extended bismaleimides of the invention. Adhesive compositions containing the chain-extended bismaleimides of the invention can also include at least one of an epoxy, an oxetane, a phenol, a phenyl acetate, an acrylate, a methacrylate, a maleimide, a vinyl ether, a vinyl ester, a styrenic compound and an allyl functional compound. Adhesive compositions containing the chain-extended bismaleimides of the invention can also include at least one modifier selected from a polyacrylate, a poly(butadiene), a polyTHF, a carboxy-terminated butadiene-acrylonitrile rubber, and polypropylene glycol. In certain embodiments, the adhesive compositions of the invention include at least one curing initiator.

Also provided by the invention are methods of using the adhesive compositions of the invention to attach a first article to a second article, including the steps of applying the adhesive composition to the first article, the second article, or both the first and second article; bringing the first and the second article into contact to form an assembly, where the first article and the second article are separated only by the applied adhesive composition; and curing the adhesive composition, thereby attaching the first article to the second article.

In certain embodiments, the adhesive compositions of invention are B-stageable adhesives. Such B-stageable adhesive compositions can be used, for example, for attaching a die to a substrate by applying the B-stageable adhesive composition to the die, the substrate, or both the die and the substrate (e.g. by spin coating, spray coating, stencil printing, screen printing, or dispensing); melting the applied B-stageable adhesive composition; contacting the die and the substrate, such that the die and substrate are separated only by the melted B-stageable adhesive composition; and curing the B-stageable adhesive composition, thereby attaching the die to the substrate. Curing can be accomplished, for example, by heating the assembled parts containing the b-stageable adhesive composition to a temperature of about 80° C. to about 220° C.

DETAILED DESCRIPTION

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

DEFINITIONS

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated).

It should be understood that the term "di-cinnamyl compound" as used herein includes di-cinnamyl esters, di-cinnamyl amides, di-cinnamyl ethers, di-cinnamyl urethanes, and di-cinnamyl ketones. The compounds described and compositions described herein are useful as adhesive for the electronic packaging industry. The invention compositions described herein can be cured in a variety of ways with or without a catalyst.

As used herein, "aliphatic" refers to any alkyl, alkenyl, cycloalkyl, or cycloalkenyl moiety.

"Aromatic hydrocarbon," as used herein, refers to compounds having one or more benzene rings.

"Alkane," as used herein, refers to saturated straight-chain, branched or cyclic hydrocarbons having only single bonds. Alkanes have general formula $C_nH_{2n+2}$.

"Cycloalkane," refers to an alkane having one or more rings in its structure.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated). "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —C(O)O—, —S—, —S(O)$_2$—, —OC(O)—O—, —NR—C(O)—NR—, —OC(O)—NR—, wherein R is H or lower alkyl (i.e. C$_1$ to C$_{12}$ alkyl), acyl, oxyacyl, carboxyl, carbamate, sulfonyl, sulfonamide, sulfuryl, and the like.

As used herein, "cycloalkyl" refers to cyclic ring-containing groups typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above. The term heterocyclic is also intended to refer to heteroaromatic moieties.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene (CH$_2$) unit. "Substituted alkylene" and "substituted oxyalkylene" refer to alkylene and oxyalkylene groups further bearing one or more substituents as set forth above.

As used herein, "arylene" refers to a divalent aryl moiety. "Substituted arylene" refers to arylene moieties bearing one or more substituents as set forth above.

"Allyl" as used herein, refers to refers to a compound bearing at least one moiety having the structure:

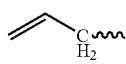

"Imide" as used herein, refers to a functional group having two carbonyl groups bound to a primary amine or ammonia. The general formula of an imide of the invention is:

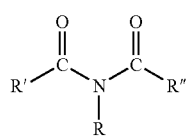

"Polyimides" are polymers of imide-containing monomers. Polyimides typically have one of two forms: linear or cyclic. Non-limiting examples of linear and cyclic (e.g. an aromatic heterocyclic polyimide) polyimides are shown below for illustrative purposes.

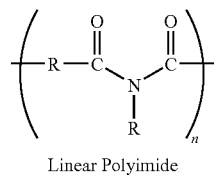

Linear Polyimide

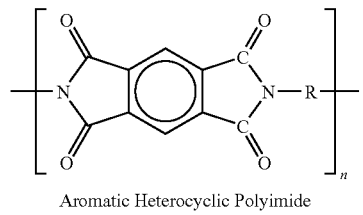

Aromatic Heterocyclic Polyimide

"Maleimide," as used herein, refers to an N-substituted maleimide having the formula as shown below:

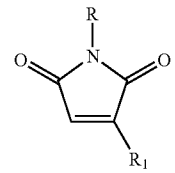

wherein the "R" group may be an aromatic, heteroaromatic, aliphatic, or polymeric moiety and where the "R$_1$" group is either hydrogen or methyl.

"Bismaleimide" or "BMI", as used herein, refers to a polyimide having the general structure shown below:

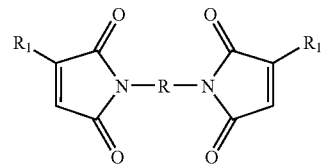

where the "R" group may be an aromatic, heteroaromatic, aliphatic, or polymeric moiety and where the "R$_1$" group is either hydrogen or methyl. BMIs can cure through an addition rather than a condensation reaction, thus avoiding problems with volatiles forming. They can be cured by a vinyl-type polymerization of a pre-polymer terminated with two maleimide groups.

As used herein, the term "cyanate ester" refers to a compound bearing at least one moiety having the structure:

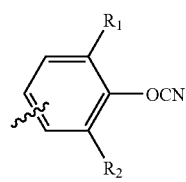

where R$_1$ and R$_2$ are independently H or Me.

As used herein, the term "acrylate" refers to a compound bearing at least one moiety having the structure:

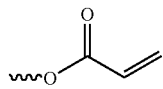

As used herein, the term "acrylamide" refers to a compound bearing at least one moiety having the structure:

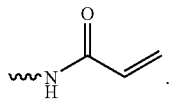

As used herein, the term "methacrylate" refers to a compound bearing at least one moiety having the structure:

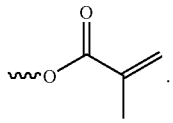

As used herein, the term "methacrylamide" refers to a compound bearing at least one moiety having the structure:

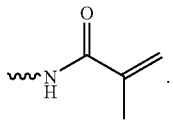

"Halogen," as used herein, includes fluorine, chlorine, bromine and iodine.

As used herein "epoxy" refers to a thermosetting epoxide polymer that cures by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof. Epoxies of the invention include compounds bearing at least one moiety having the structure:

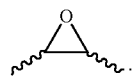

As used herein, the term "styrenic" refers to a compound bearing at least one moiety having the structure:

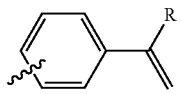

where R=H or $CH_3$.

As used herein, the term "oxetane" refers to a compound bearing at least one moiety having the structure:

As used herein, the term "vinyl ether" refers to a compound bearing at least one moiety having the structure:

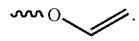

"Adhesive" or "adhesive compound" as used herein, refers to any substance that can adhere or bond two items together. Implicit in the definition of an "adhesive composition" or "adhesive formulation" is the fact that the composition or formulation is a combination or mixture of more than one species, component or compound, which can include adhesive monomers, oligomers, and/or polymers along with other materials, whereas an "adhesive compound" refers to a single species, such as an adhesive polymer or oligomer.

More specifically, adhesive composition refers to un-cured mixtures in which the individual components in the mixture retain the chemical and physical characteristics of the individual components of which the mixture is made. Adhesive compositions are typically malleable and may be liquids, paste, gel or another form that can be applied to an item so that it can be bonded to another item.

"Cured adhesive," "cured adhesive composition" or "cured adhesive compound" refers to adhesives components and mixtures which have undergone a chemical and/or physical changes such that the mixtures is transformed into a solid, substantially non-flowing material which curing process may involve e.g. crosslinking.

"Curable" means that a compound or composition material can be transformed into a solid, substantially non-flowing material by means of chemical reaction (e.g. Michael addition) crosslinking, radiation crosslinking, or the like. Thus, adhesive compositions of the invention are curable, but unless otherwise specified, are not cured.

"Glass transition temperature" or "$T_g$," is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

"Thermoplastic," as used herein, refers to the ability of a compound, composition or other material (e.g. a plastic) to melt to a liquid when heated and freeze to a solid, often brittle and glassy, state when cooled sufficiently.

"Thermoset," as used herein, refers to the ability of a compound, composition or other material to irreversibly "cure" to a stronger, harder form. Thermoset materials are typically polymers that may be cured, for example, through heat (e.g. above 200 degrees Celsius, or less than 200° C. in the presence of a suitable catalyst), via a chemical reaction (e.g. epoxy), or through irradiation (e.g. U.V. irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible solid or rubber by a cross-linking process. Thus, energy and/or catalysts are added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

"Cross-linking," as used herein, refers to the attachment of two or more polymer chains by bridges of an element, a molecular group, or a compound. In general, crosslinking of the compounds of the invention takes place upon heating. As cross-linking density is increased, the properties of a material can be changed from thermoplastic to thermosetting.

As used herein, "B-stageable" refers to the properties of an adhesive having a first solid phase followed by a tacky rubbery stage at elevated temperature, followed by yet another solid phase at an even higher temperature. The transition from the tacky rubbery stage to the second solid phase is thermosetting. However, prior to thermosetting, the material behaves similarly to a thermoplastic material. Thus, such adhesives allows for low lamination temperatures while providing high thermal stability.

A "die" as used herein, refers to a small block of semiconducting material, on which a functional circuit is fabricated.

The invention is based on the discovery that di-cinnamyl compounds can be used to chain-extend bismaleimide resins. This permits the generation of new, higher molecular weight, maleimide-terminated, compounds. This approach provides a new level of control over cross-link density for maleimide thermosets. In some applications it also allows brittle, high melting bismaleimides (BMIs) to be converted into adhesive B-staged, film-forming oligomers. This is particularly attractive for use in film or pre-applied adhesives. These "cinnamyl extended" BMI resins can be made by simply heating a desired stoichiometric ratio (wherein the BMI is always used in molar excess) of a di-cinnamyl compound (or a combination of bis-cinnamyl compounds) and a bismaleimide (or a combination of bismaleimides). The di-cinnamyl compound thus allows BMI resins to be "B-staged".

The di-cinnamyl compounds and compositions described herein, and in particular the chain-extended bismaleimide derivatives of these compounds, are broadly useful as thermoset resins, coatings and adhesives. The compounds, compositions and methods of the invention are therefore also valuable in a variety of applications in addition to the microelectronic packaging industry. Invention compounds, compositions and methods can be used, for example, in automotive, marine, and aerospace coatings and adhesives. The properties of certain invention compounds and compositions make these compounds suitable for use in high performance composites and adhesives for use in the assembly of aerospace assemblies. Invention compounds and compositions can also be used as components of matrix resins for composites used in sports equipment, automotive bodies, and boat construction. The compounds, compositions and methods of this invention also have attractive properties for use in adhesives for diverse industrial applications such as thread-lock materials and building materials. The invention compounds, compositions and methods are also attractive for the bonding of metal to rubber where high heat resistance is required.

Thus, the present invention provides methods for preparing chain-extended bismaleimides including the steps of mixing a molar excess of at least one bismaleimide with at least one di-cinnamyl compound; and heating the mixture of step (a), thereby preparing a chain-extended bismaleimide. The di-cinnamyl compound can be a di-cinnamyl ester, di-cinnamyl amide, di-cinnamyl ether, di-cinnamyl urethane, or a di-cinnamyl ketone.

The present invention also provides di-cinnamyl compounds that can be used in the methods of the invention. In certain embodiments, the di-cinnamyl compound of the invention has a structure of formula I:

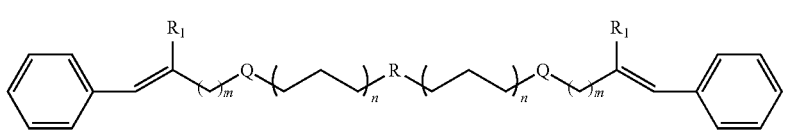

where each Q is independently —C(O)O—, —C(O)NH—, —OC(O)O—, —O—, —OC(O)—, —NHC(O)—, or —OC(O)NH—; R is a substituted or unsubstituted $C_2$ to $C_{100}$ aliphatic, heteroaliphatic, cycloaliphatic, branched aliphatic, branched hetero aliphatic, heterocyclic, heteroaromatic, aryl, polyaryl or a silicone containing 2-20 silicon atoms optionally substituted with one or two methyl or phenyl groups; each $R_1$ is independently H or Me; each m is independently 0 or 1; and each n is independently 0 or 1.

Typically, R is a $C_2$ to $C_{100}$ aliphatic or heteroaliphatic spacer group such as a $C_2$ to $C_{100}$, $C_5$ to $C_{100}$, $C_{10}$ to $C_{100}$, $C_{20}$ to $C_{100}$, $C_{50}$ to $C_{100}$, $C_2$ to $C_{75}$, $C_2$ to $C_{50}$, $C_2$ to $C_{20}$, or $C_2$ to $C_{10}$ aliphatic or heteroaliphatic. In some embodiments, the spacer is cycloaliphatic or heterocycloaliphatic containing 3 to 100 carbon atoms, typically 4 to 75 carbon atoms, frequently 5 to 50 carbon atoms, and most often, 6 to 20 carbon atoms. In other embodiments, the spacer is a branched aliphatic or branched heteroaliphatic, such as a $C_3$ to $C_{100}$, $C_5$ to $C_{100}$, $C_{10}$ to $C_{100}$, $C_{20}$ to $C_{100}$, $C_{50}$ to $C_{100}$, $C_2$ to $C_{75}$, $C_3$ to $C_{50}$, $C_2$ to $C_{20}$, or $C_3$ to $C_{10}$ branched aliphatic or branched heteroaliphatic. In one embodiment, the spacer is a $C_{36}$ branched aliphatic moiety. In still further embodiments, the spacer is a heterocyclic moiety or a heteroaromatic moiety having from 3 to about 100 carbon atoms, such as a $C_3$ to $C_{100}$, $C_5$ to $C_{100}$, $C_{10}$ to $C_{100}$, $C_{20}$ to $C_{100}$, $C_{50}$ to $C_{100}$, $C_3$ to $C_{75}$, $C_3$ to $C_{50}$, $C_3$ to $C_{20}$, or $C_3$ to $C_{10}$ heterocyclic or heteroaromatic; or an aryl moiety or polyaryl moeity having from 6 to about 100 carbon atoms, such as a $C_6$ to $C_{100}$, $C_8$ to $C_{100}$, $C_{10}$ to $C_{100}$, $C_{20}$ to $C_{100}$, $C_{50}$ to $C_{100}$, $C_6$ to $C_{75}$, $C_6$ to $C_{50}$, $C_6$ to $C_{20}$, or $C_6$ to $C_{10}$ aryl or polyaryl.

In other embodiments, the di-cinnamyl has a structure of formula II:

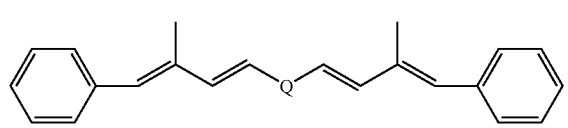

where Q is —C(O)—.

Representative, non-limiting examples of di-cinnamyl of the invention are shown below:
Compound 1
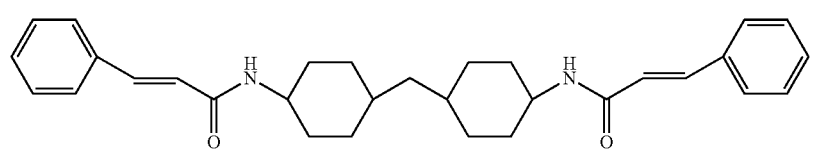
Compound 2
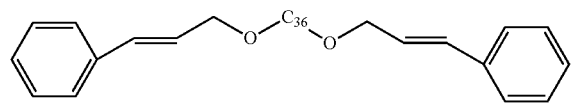
Compound 3
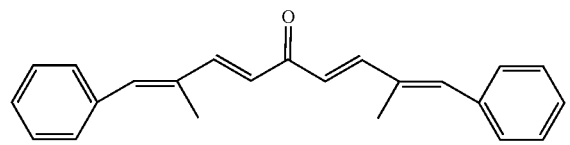
Compound 4
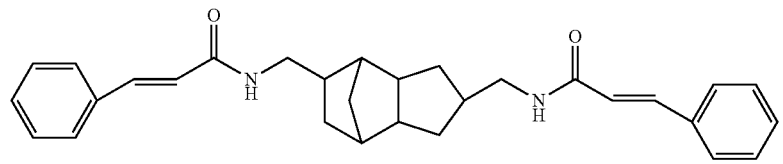
Compound 5
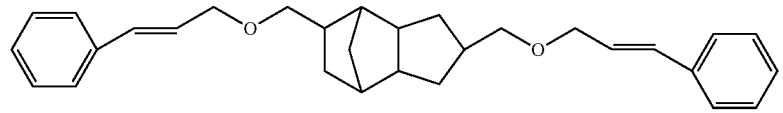
Compound 6
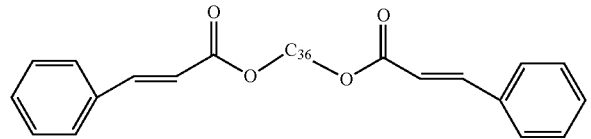
Compound 7
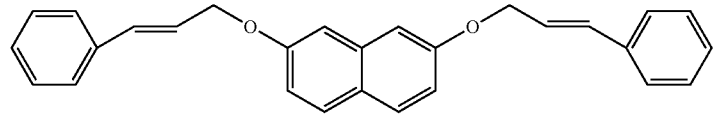
Compound 8
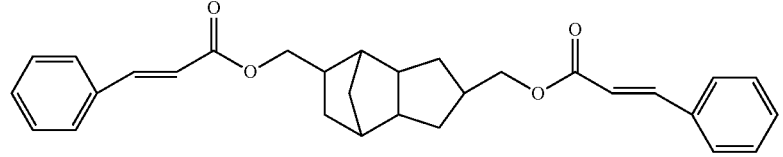
Compound 9
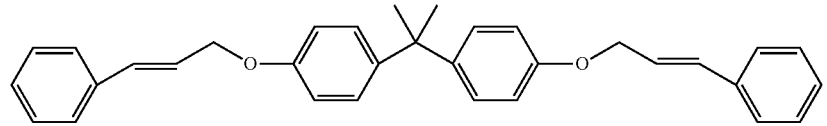
Compound 10
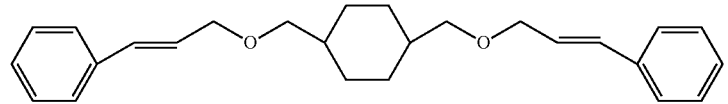
Compound 11
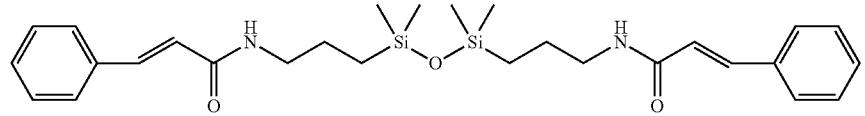

Compound 12

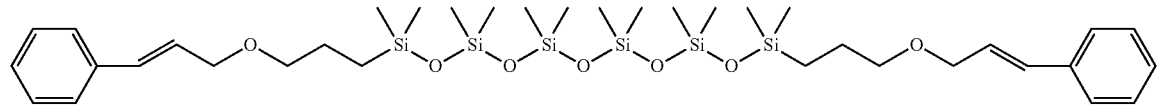

The invention also provides chain-extended bismaleimides prepared according to the methods of the invention and adhesive compositions containing the chain-extended bismaleimide. Such adhesive compositions can include at least one of an epoxy, an oxetane, a phenol, a phenyl acetate, an acrylate, a methacrylate, a maleimide, a vinyl ether, a vinyl ester, a styrenic compound or an allyl functional compound.

In certain embodiments, the adhesive compositions according to the invention include at least one modifier selected from a polyacrylate, a poly(butadiene), a polyTHF, a carboxy-terminated butadiene-acrylonitrile rubber, and polypropylene glycol.

In yet further embodiments, the adhesive compositions include a curing initiator and/or may be B-stageable adhesives.

In yet another embodiment, the present invention provides methods for increasing the adhesiveness (i.e. adhesion or adhesive strength) of a bismaleimide including the steps of mixing a molar excess of at least one bismaleimide with at least one di-cinnamyl compound, and heating the mixture, thereby increasing the adhesive strength of the cured bismaleimide. In certain embodiments, the adhesive strength will be increased by 10-75%. Typically, this method increases the adhesive strength by at least about 10%, frequently by at least about 25%, often by at least about 50% and can increase the adhesive strength by at least about 65% or more.

The present invention also provides methods for reducing the brittleness of a bismaleimide thermoset including the steps of mixing a molar excess of at least one bismaleimide with at least one di-cinnamyl compound; heating the mixture in order to generate a chain-extended bismaleimide monomer, and curing this chain-extended bismaleimide monomer to produce a thermoset that possess improved toughness (i.e. which is less brittle than a cured sample of the original non-chain extended bismaleimide resin).

BMI resin thermosets are considered to be high performance adhesives and/or matrix resins in terms of their heat resistance and glass transition temperatures but suffer from excessive brittleness. BMI-containing resins are therefore limited in terms of their potential range of practical applications because of the inherent brittleness of cured adhesives prepared from them. The chain extension approach described herein can also be used to tailor lower cross-link densities and is an effective method to improve the toughness of the bismaleimide-based thermoset compositions. Thus, the use of the invention compounds for chain-extension has the advantage of reducing brittleness in the final thermoset.

While not wishing to be bound by a particular theory, it is believed that the di-cinnamyl compounds of this invention chain-extend the BMI monomers via Diels-Alder addition. Thus, the maleimide functional group adds across the conjugated, exocyclic double bond of the cinnamyl residue and unsaturation within the aromatic ring. Presumably, the olefinically substituted, cyclohexadiene intermediates that form rearrange and re-form an aromatic ring structure without further reaction with another maleimide moiety. It is therefore possible to convert combinations of bismaleimide and di-cinnamyl compounds into solvent soluble, thermoplastic compounds that can subsequently be cured into thermosets.

The invention provides novel di-cinnamyl compounds and cinnamyl-extended BMIs useful in a variety of adhesive applications. In certain embodiments, invention di-cinnamyl compounds can be used as co-monomers in a Diels-Alder type cure. For example, the di-cinnamyl monomer compounds described herein can act as co-monomers in a thermoset composition with a mono-, bis-, or polymaleimide monomer. In some embodiments, the thermoset compositions contain bismaleimide resins, that may, under certain conditions, undergo chain-extension by the di-cinnamyl monomer. In further embodiments the di-cinnamyl monomers described herein can be pre-reacted with bismaleimide resins to form B-staged thermosetting resins.

In other embodiments, the invention provides adhesive compositions including di-cinnamyl monomer compounds and chain-extended bismaleimides described herein and optionally at least one curing initiator. These di-cinnamyl compounds are useful as thermosetting monomers that can be incorporated into adhesive compositions. In some embodiments, the adhesive compositions are useful in the microelectronic packaging industry.

In still other embodiments, the present invention provides adhesive compositions that are die-attach pastes which include 5 weight percent to about 85 weight percent (wt %) of at least one di-cinnamyl compound described herein, based on total weight of the composition; 10 wt % to about 90 wt % of at least one maleimide, bismaleimide, or polymaleimide, based on the total weight of the composition; 0 weight percent to about 60 weight percent of a compound selected from acrylates, methacrylates, acrylamides, methacrylamides, cyanate esters, vinyl ethers, vinyl esters, styrenic compounds and allyl functional compounds; 0 to about 90 wt % of a filler; 0 wt % to about 5 wt % of at least one curing initiator, based on total weight of the composition; 0.1 wt % to about 4 wt %, of at least one coupling agent, based on total weight of the composition.

In certain embodiments, the adhesive compositions include 10 wt % to about 50 wt % of at least one compound described herein, based on total weight of the composition; 20 wt % to about 70 wt % of at least one maleimide, bismaleimide, or polymaleimide, based on the total weight of the composition; 2 wt % to about 25 wt % of a compound selected from acrylates, methacrylates, maleimides, vinyl ethers, vinyl esters, styrenic compounds or allyl functional compounds; 0 to about 90 wt % of a filler; 0 wt % to about 5 wt % of at least one curing initiator, based on total weight of the composition; and 0.1 wt % to about 4 wt %, of at least one coupling agent, based on total weight of the composition. In certain embodiments, the acrylates and methacrylates, when present in the adhesive compositions of the invention, are selected from neopentyl glycol diacrylate, 1,4-butanediol diacrylate, 1,6-hexanediol diacrylate, cyclohexane dimethanol diacrylate, ethoxylated bisphenol A diacrylate, tricyclodecane dimethanol diacrylate, dicyclopentadiene acrylate, neopentyl glycol dimethacrylate, 1,4-butanediol dimethacrylate, 1,6-hexanediol dimethacrylate, cyclohexane dimethanol dimethacrylate, ethoxylated bisphenol A dimethacrylate, tricyclodecane dimethanol dimethacrylate, and dicyclopentadiene methacrylate.

In some embodiments, there is at least one curing initiator present in the adhesive composition, from 0.1 wt % to about 5 wt %. In some embodiments, the curing initiator is a free-radical initiator. As used herein, the term "free radical initiator" refers to any chemical species which, upon exposure to sufficient energy (e.g., light, heat, or the like), decomposes into two parts which are uncharged, but which each posses at least one unpaired electron. Preferred free radical initiators contemplated for use in the practice of the present invention are compounds which decompose (i.e., have a half life in the range of about 10 hours) at temperatures in the range of about 70° C. up to 180° C. Free radical initiators are well known in the art. Exemplary free radical initiators suitable for use in the practice of the present invention include, but are not limited to, peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide).

The term "free radical initiator" also includes photoinitiators. When invention adhesive compositions contain a photoinitiator, the curing process can be initiated, for example, by UV radiation. In one embodiment, the photoinitiator is present at a concentration of 0.1 wt % to 5 wt % based on the total weight of the organic compounds in the adhesive composition (excluding any filler). In certain embodiments, the photoinitiator comprises 0.1 wt % to 3.0 wt %, based on the total weight of the organic compounds in the adhesive composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In further embodiments, the adhesives of the present invention that include at least one invention compound, may be suitable for use as die-attach adhesives, such as die attach pastes. Die attach adhesives represent a subset of adhesive compositions suitable for use in the electronics field, particularly for bonding dies e.g. to substrates or metal lead frames. Typically, die attach adhesives are pastes, but they may also be pre-applied, B-staged thermoplastic formulations or films.

The die-attach adhesives described herein may further contain additional compounds. Such compounds include, for example, epoxies, phenolics [such as novolacs, or resoles (both phenolic and cresolic) and the like], imides, monomaleimides, bismaleimides, polymaleimides, cyanate esters, vinyl ethers, vinyl esters, vinyl acetates, olefins, cyanoacrylates, styrenics, oxazolines, benzoxazines, oxetanes, and the like, or combinations thereof.

In some embodiments, fillers are contemplated for use in the practice of the present invention. These can be electrically conductive and/or thermally conductive. In addition, the fillers may act to modify the rheology of the resulting composition. Examples of suitable electrically conductive fillers that can be employed in the practice of the present invention include, but are not limited to, silver, nickel, copper, silver coated copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds that act primarily to modify rheology include polysiloxanes (such as polydimethyl siloxanes) silica, calcium carbonate, polytetrafluoroethylene, fumed silica, alumina, titania, and the like.

As used herein, the term "coupling agent" refers to chemical species that are capable of covalently bonding to a mineral surface and which also contain polymerizably reactive functional group(s) so as to enable a bond forming interaction with the adhesive composition and/or die-attach paste. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, epoxy moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

In general, the adhesive compositions and/or die-attach pastes will cure within a temperature range of 80-220° C., and curing will be effected within a length of time of less than about 1 minute to about 60 minutes. As will be understood by those skilled in the art, the time and temperature curing profile for each adhesive composition will vary, and different compositions can be designed to provide the curing profile that will be suited to the particular industrial manufacturing process.

In certain embodiments, the adhesive compositions and/or die-attach adhesives may contain compounds that lend additional flexibility and toughness to the resultant cured adhesive. Such compounds may be any thermoset or thermoplastic material having a $T_g$ of 50° C. or less, and typically will be a polymeric material characterized by free rotation about the chemical bonds, the presence of ether groups, and the absence of ring structures. Suitable such modifiers include, but are not limited to, polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of the maleimide and other monofunctional vinyl compound.

Inhibitors for free-radical cure may also be added to the adhesive compositions and die-attach pastes described herein to extend the useful shelf life of compositions containing the di-cinnamyl compounds and/or extended-bismaleimides described herein. Examples of these inhibitors include hindered phenols such as 2,6-di-tert-butyl-4-methylphenol; 2,6-di-tert-butyl-4-methoxyphenol; hydroquinone, 4-methoxyphenol, tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants include derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine.

Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

In yet another embodiment of the invention, the present invention provides assemblies of components adhered together employing the above-described adhesive compositions and/or die attach adhesives. Thus, for example, assemblies comprising a first article permanently adhered to a second article by the adhesives described herein are provided. Articles contemplated for assembly employing invention compositions include memory devices, ASIC devices, microprocessors, flash memory devices, and the like. Also contemplated are assemblies comprising a microelectronic device permanently adhered to a substrate by the above-described die attach adhesives. Microelectronic devices contemplated for use with invention die attach pastes include copper lead frames, Alloy 42 lead frames, silicon dice, gallium arsenide dice, germanium dice, and the like.

Also provided by the invention are methods for attaching a first article to a second article, including the steps of applying an adhesive composition of the invention to the first article, the second article, or both the first and second article; bringing the first and the second article into contact to form an assembly, where the first article and the second article are separated only by the applied adhesive composition; and curing the adhesive composition, thereby attaching the first article to the second article.

In certain embodiments, the invention provides methods for attaching a die to a substrate including the steps of applying a B-stageable adhesive composition of the invention to the die, the substrate, or the die and the substrate; melting the applied B-stageable adhesive composition; contacting the die and the substrate, such that the die and substrate are separated only by the melted B-stageable adhesive composition; and curing the B-stageable adhesive composition such as by heating to a temperature of about 80° C. to about 220° C., thereby attaching the die to the substrate. In certain embodiments of the invention, applying the B-stageable adhesive can include such methods by spin coating, spray coating, stencil printing, screen printing, or dispensing.

EXAMPLES

Example 1

Synthesis of Compound 8

A 125 ml, single neck flask was charged with 9.86 g (0.050 mole) tricyclopentanedimethanol, 15.51 g (0.105 mole) trans-cinnamic acid, 50 ml toluene, and 0.5 g methanesulfonic acid. The flask was equipped with a magnetic stir bar, Dean-Stark trap and condenser. The mixture was refluxed for 3.5 hours to collect the expected 1.8 ml water. The residual acid was neutralized with 7.2 g sodium bicarbonate and the solution was passed over 24.5 g silica gel. The toluene was removed under vacuum in a rotary evaporator followed by an air sparge. The product was recovered as a clear, viscous, tacky, amber liquid. It weighed 22.66 g (99.0% of theory). An FTIR spectrum of the compound revealed significant absorptions at 2956, 1704, 1637, 1449, 1309, 1201, 1161, 978, 863, 767, and 684 wavenumbers.

Example 2

Synthesis of Compound 6

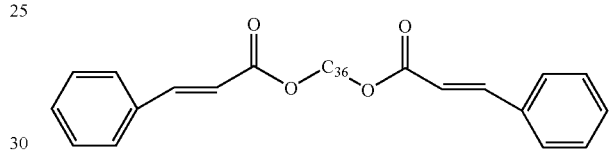

A 500 ml, single neck flask was charged with 15.6 g (0.105 mole) trans-cinnamic acid, 26.8 g (0.050 mole) dimerdiol (Solvermol 908 from the Cognis Corporation, Cincinnati, Ohio), 100 ml toluene, and 0.5 g methanesulfonic acid. The flask was equipped with a magnetic stir bar, a Dean-Stark trap, and a condenser. The mixture was allowed to reflux overnight and 1.7 ml (1.8=theoretical) water was collected in the trap. The mixture was cooled and neutralized by stirring it with 7.9 g sodium bicarbonate and 3.3 g water. The mix was dried with 7.5 g anhydrous magnesium sulfate and then passed over 24.0 g silica gel, along with toluene rinses. The toluene was removed under vacuum on a rotary evaporator and then the last traces of solvent were removed via an air sparge. The product was recovered as a red-amber, moderately viscous liquid. It weighed 37.6 g (94.5% of theory). A TGA run on the neat compound revealed 99.6% of the original compound was still retained at 250° C., and a decomposition onset of 361° C. An FTIR on this compound revealed prominent absorptions at 2927, 2854, 1713, 1638, 1450, 1308, 1165, 978, 863, and 766 wavenumbers.

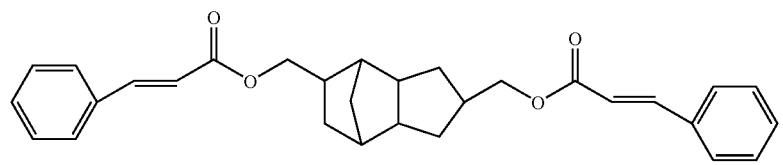

Example 3

Synthesis of Compound 9

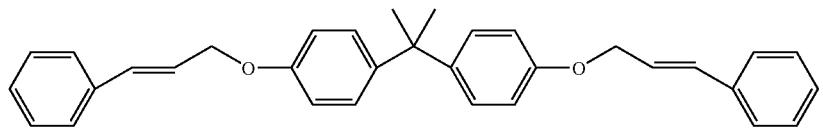

A 125 ml, single neck flask was charged with 8.04 g (0.0408 mole) bisphenol A, 4.0 g (0.10 mole) NaOH, 4.3 g water, and 25 ml toluene. This mixture was swirled for a few minutes in order to completely dissolve the NaOH. The flask was then charged with 4.58 g (0.020 mole) cinnamyl bromide and 0.25 g tetrabutylphosphonium bromide. The mixture was then stirred magnetically at room temperature for two hours. An FTIR on the toluene phase suggested that the reaction was complete. The lower phase was removed and the toluene solution was stirred with 5.4 g anhydrous magnesium sulfate for twenty minutes. The mix was then filtered through a fine frit and the solids rinsed with additional toluene. The toluene was removed to yield a light yellow solid. This solid was recrystallized from a mixture of acetone and isopropyl alcohol to yield a first crop of white crystals that weighed 5.14 g (56% of theory). A DSC on this compound (at a ramp rate of 10° C./minute) revealed a symmetric melt with an onset at 117.7° C. and a minimum at 121.1° C. The FTIR spectrum for this compound had prominent absorptions at 1606, 1508, 1376, 1235, 1152, 1009, 956, 827, 745, and 690 wavenumbers.

Example 4

Synthesis of Compound 2

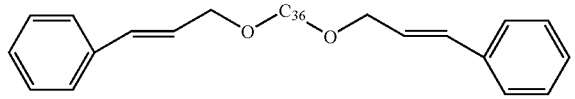

A 125 ml, single neck flask was charged with 8.05 g (0.015 mole) dimerdiol, 6.06 g (0.0307 mole) cinnamyl bromide, 4 g (0.1 mole) NaOH, 25 g toluene, and 0.2 g tetrabutylphosphonium bromide. This mixture was stirred magnetically overnight. The mixture was then filtered and the solids rinsed with additional toluene. The toluene was then removed to yield 10.9 g (94.4% of theory) of a light yellow, mobile liquid. This compound was found to have prominent absorptions in the FTIR spectrum at 2923, 2852, 1457, 1362, 1110, 964, 741, and 691 wavenumbers.

Example 5

Demonstration of Synergistic Cure Between Cinnamate and Maleimide Functional Groups A 1:1 equivalent mixture of Compound 8 from Example 1 and X-BMI (see Example 1 from U.S. Pat. No. 6,034,194, incorporated by reference herein) was prepared. A DSC (air purge, 10° C./minute ramp rate) trace was run on this uncatalyzed mixture. A symmetric exotherm was observed with an onset starting at 151.2° C. and a cure maxima at 174.7° C. The cure energy was 282 J/g. A DSC run on the neat Compound 8 did not demonstrate evidence of a cure up through the end of the run at 300° C. A portion of the compound from Example 1 was catalyzed with two percent dicumyl peroxide. This catalyzed mixture did demonstrate a modest (29.2 J/g) cure with a maxima at 186.8° C. The X-BMI with 2% dicumyl peroxide, cured by itself, had a cure energy of 224 J/g with a cure maxima at 147.4° C. The X-BMI cured in the absence of a free radical catalyst had a broad exotherm centered at 238.6° C. with a cure energy of 163 J/g.

The 1:1 equivalent ratio of Compound 8 and X-BMI contained 40% by weight of the dicinnamate and 60% by weight of the bismaleimide. The cure energy for the mix was significantly higher for this mix than for either of the component monomers (catalyzed or uncatalyzed). The cure onset and maxima for the uncatalyzed mixture was dramatically different from that of the component monomers. This behavior indicated that a synergistic cure mechanism between the cinnamate and maleimide functional groups was occurring.

Example 6

Adhesiveness Testing of BMI Extended with 2:1 Ratio of BMI to Compound 6

A mixture was made consisting of 1.0 millimole of Compound 6 from Example 2 and 2.0 millimoles bis(4-maleimidophenyl)methane. This mixture was stirred and heated at 150° C. for twenty minutes. The mix was observed to solidify to a yellow waxy solid on cooling. The mixture was then re-heated to 150° C. and maintained at this temperature for another two hours with occasional stirring. The mix appeared upon cooling to be a homogeneous, red, thermoplastic solid. It was possible to pull strings of the material from the mixture as it cooled. This behavior suggested that chain extension was occurring. The mix was then mixed with two percent by weight dicumyl peroxide. This thermoplastic composition was used to attach aluminum studs (0.177 inch head diameter) to copper slugs. A control consisting of X-BMI catalyzed with two percent dicumyl peroxide was also used to prepare adhesion test fixtures. The test and control parts were then cured at 200° C. for one hour. The parts were then tested for tensile strength using a Sebastian III stud pull machine. The results of this test are shown in Table 1.

TABLE 1

Tensile Test Results 6

| Part | 2:1 BMI:Compound 6 + 2% DCP Adhesion (pounds Force) | X-BMI + 2% DCP Adhesion (pounds force) |
|---|---|---|
| 1 | 32 | 17 |
| 2 | 32 | 26 |

TABLE 1-continued

Tensile Test Results 6

| Part | 2:1 BMI:Compound 6 + 2% DCP Adhesion (pounds Force) | X-BMI + 2% DCP Adhesion (pounds force) |
|---|---|---|
| 3 | 27 | 20 |
| 4 | 26 | 30 |
| 5 | 29 | 24 |
| 6 | 38 | 16 |
| 7 | 37 | 17 |
| 8 | 44 | 10 |
| 9 | 34 | 25 |
| 10 | 31 | 20 |
| Average | 33.0 | 20.5 |
| Std. Dev. | 5.5 | 5.9 |

The adhesion for the test composition was about 61% greater than that of the control.

Example 7

Adhesiveness Testing of BMI Extended with 5:4 Ratio of BMI to Compound 6

A similar test to the one described in Example 6 was performed using Compound 6 from Example 2. A mixture was made consisting of 4.0 millimole of the Compound 6, 5.0 millimoles bis(4-maleimidophenyl)methane, and 2000 ppm 4-methoxyphenol (inhibitor). This mix was heated at 150° C. with periodic stirring for ten hours. The product formed an apparently homogeneous, red, compliant thermoplastic film when cooled. It was possible to pull long strings of the material from the mixture as it cooled. This behavior suggested that chain extension was occurring. The chain-extended product was then mixed with two percent by weight dicumyl peroxide. This thermoplastic composition was used to attach aluminum studs (0.177 inch head diameter) to copper slugs. A control consisting of X-BMI catalyzed with two percent dicumyl peroxide was also used to prepare adhesion test fixtures. The test and control parts were then cured at 200° C. for one hour. The parts were then tested for tensile strength using a Sebastian III stud pull machine. The results of this test are shown in Table 2.

TABLE 2

Tensile Test Results

| Part | 5:4 BMI:Compound 6 + 2% DCP Adhesion (pounds Force) | X-BMI + 2% DCP Adhesion (pounds force) |
|---|---|---|
| 1 | 49 | 37 |
| 2 | 64 | 38 |
| 3 | 57 | 39 |
| 4 | 40 | 37 |
| 5 | 34 | 50 |
| 6 | 45 | 21 |
| 7 | 42 | 39 |
| 8 | 64 | 54 |
| 9 | 54 | 25 |
| 10 | 40 | 53 |
| Average | 49.0 | 39.3 |
| Std. Dev. | 10.5 | 10.9 |

The adhesion for the test composition was about 25% greater than that of the control.

What is claimed is:

1. A method for preparing a chain-extended bismaleimide comprising:
   a) mixing a molar excess of at least one bismaleimide with at least one di-cinnamyl compound; and
   b) heating the mixture of step (a), thereby preparing a chain-extended bismaleimide,
   wherein the at least one di-cinnamyl compound is selected from the group consisting of a di-cinnamyl ester, a di-cinnamyl amide, a di-cinnamyl ether and a di-cinnamyl ketone, the at least one di-cinnamyl compound having the structure of formula I:

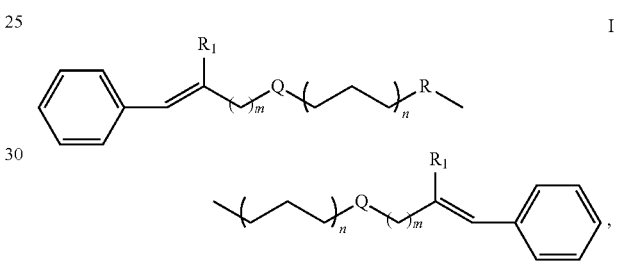

wherein:
   each Q is independently selected from the group consisting of —C(O)O—, —C(O)NH—, —OC(O)O—, —O—, —OC(O)— and —NHC(O)—;
   R is selected from the group consisting of a substituted or unsubstituted $C_2$ to $C_{100}$ aliphatic or heteroaliphatic, a $C_3$ to $C_8$ cycloaliphatic, a branched aliphatic, a branched hetero aliphatic, a heterocyclic, a heteroaromatic, an aryl, a polyaryl and a silicone containing 2-20 silicon atoms optionally substituted with one or two methyl or phenyl groups;
   each $R_1$ is independently selected from the group consisting of H and methyl;
   each m is an integer independently having the value of 0 or 1; and
   each n is an integer independently having the value of 0 or 1.

2. The method of claim 1, wherein R is a $C_3$ to $C_8$ cycloaliphatic.

3. The method of claim 1, wherein R is a $C_3$ to $C_{100}$ branched aliphatic.

4. The method of claim 1, wherein R is a $C_{36}$ branched aliphatic moiety.

5. The method of claim 1, wherein the at least one di-cinnamyl compound is selected from the group consisting of

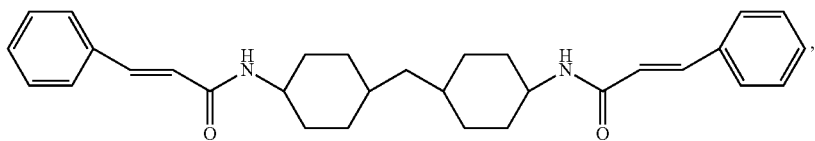

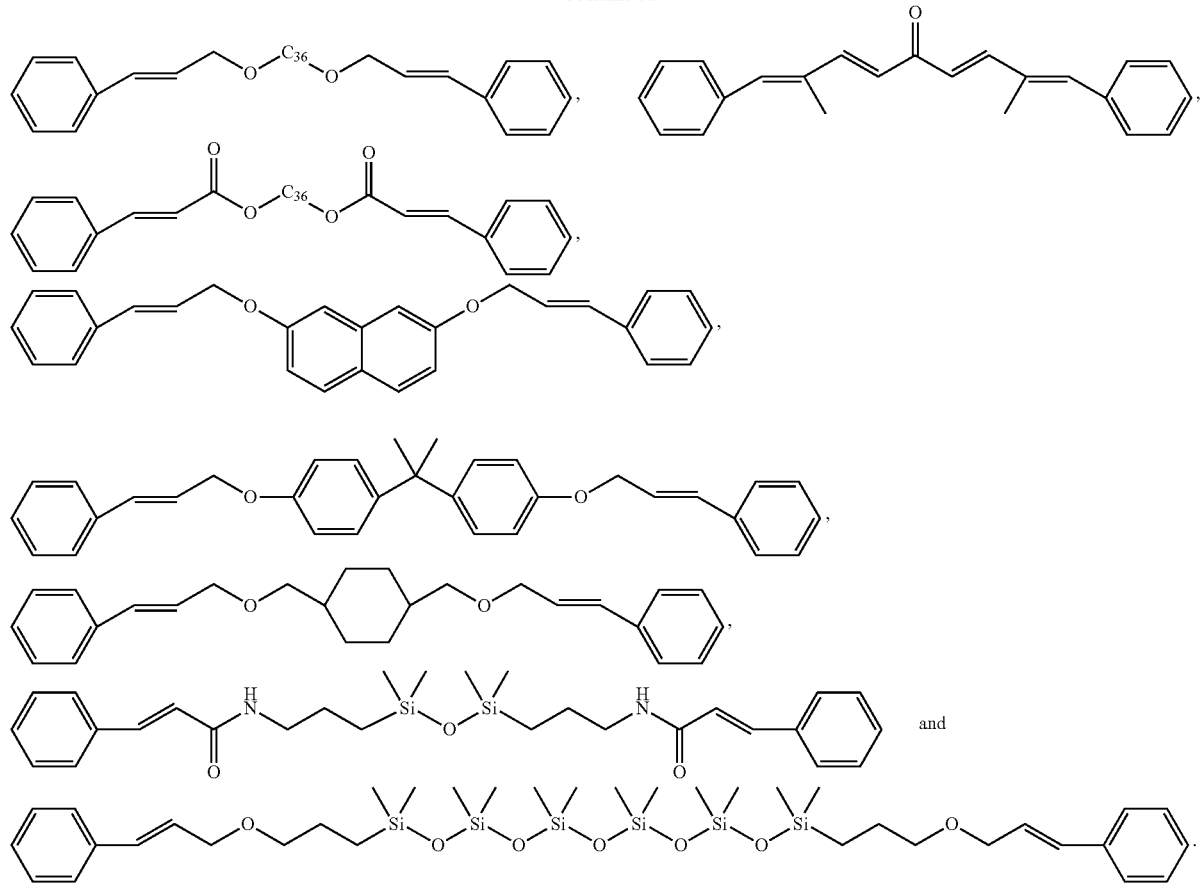

6. A chain-extended bismaleimide prepared according to the method of claim 1.

7. An adhesive composition comprising the chain-extended bismaleimide of claim 6.

8. The adhesive composition of claim 7, further comprising at least one of an epoxy, an oxetane, a phenol, a phenyl acetate, an acrylate, a methacrylate, a maleimide, a vinyl ether, a vinyl ester, a styrenic compound or an allyl functional compound.

9. The adhesive composition of claim 7, further comprising at least one modifier selected from a polyacrylate, a poly(butadiene), a polyTHF, a carboxy-terminated butadiene-acrylonitrile rubber, and polypropylene glycol.

10. The adhesive composition of claim 7, further comprising at least one curing initiator.

11. The adhesive composition of claim 7, wherein the composition is a B-stageable adhesive.

12. A method for attaching a first article to a second article, comprising:
a) applying the adhesive composition of claim 7 to the first article, the second article, or both the first and second article;
b) bringing the first and the second article into contact to form an assembly, wherein the first article and the second article are separated only by the adhesive composition applied in step (a); and
c) curing the adhesive composition, thereby attaching the first article to the second article.

13. A method for attaching a die to a substrate comprising:
a) applying the B-stageable adhesive composition of claim 11 to the die, the substrate, or both the die and the substrate;
b) melting the B-stageable adhesive composition applied in step (a);
c) contacting the die and the substrate, wherein the die and substrate are separated only by the melted B-stageable adhesive composition applied in step (a); and
d) curing the B-stageable adhesive composition, thereby attaching the die to the substrate.

14. The method of claim 13, wherein applying comprises spin coating, spray coating, stencil printing, screen printing, or dispensing.

15. The method of claim 13, wherein curing comprises heating to a temperature of about 80° C. to about 220° C.

16. A method for reducing the brittleness of a cured bismaleimide thermoset, comprising:
(a) mixing a molar excess of at least one bismaleimide with at least one di-cinnamyl compound, thereby producing a bismaleimide thermoset mixture;
(b) heating the bismaleimide thermoset mixture of step (a), thereby chain-extending the bismaleimide in the bismaleimide thermoset mixture; and
(c) curing the chain-extended bismaleimide thermoset mixture, thereby reducing the brittleness of the cured bismaleimide thermoset
wherein the at least one di-cinnamyl compound is selected from the group consisting of a di-cinnamyl ester, a di-cinnamyl amide, a di-cinnamyl ether and a di-cinnamyl ketone, the at least one di-cinnamyl compound having the structure of formula I:

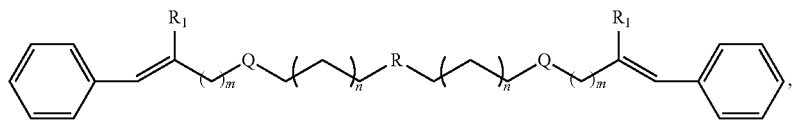

wherein:
each Q is independently selected from the group consisting of —C(O)O—, —C(O)NH—, —OC(O)O—, —O—, —OC(O)— and —NHC(O)—;
R is selected from the group consisting of a substituted or unsubstituted $C_2$ to $C_{100}$ aliphatic or heteroaliphatic, a $C_3$ to $C_8$ cycloaliphatic, a branched aliphatic, a branched hetero aliphatic, a heterocyclic, a heteroaromatic, an aryl, a polyaryl and a silicone containing 2-20 silicon atoms optionally substituted with one or two methyl or phenyl groups;
each $R_1$ is independently selected from the group consisting of H and methyl;
each m is an integer independently having the value of 0 or 1; and
each n is an integer independently having the value of 0 or 1.

17. A method for increasing the adhesion of a cured bismaleimide thermoset comprising:
(a) mixing a molar excess of at least one bismaleimide with at least one di-cinnamyl compound, thereby producing a bismaleimide thermoset mixture;
(b) heating the mixture of step (a), thereby chain-extending the bismaleimide in the bismaleimide thermoset mixture thermoset mixture; and
(d) curing the chain-extended bismaleimide thermoset mixture, thereby reducing the brittleness of the cured bismaleimide thermoset,
wherein the at least one di-cinnamyl compound is selected from the group consisting of a di-cinnamyl ester, a di-cinnamyl amide, a di-cinnamyl ether, and a di-cinnamyl ketone, the at least one di-cinnamyl compound having the structure of formula I:

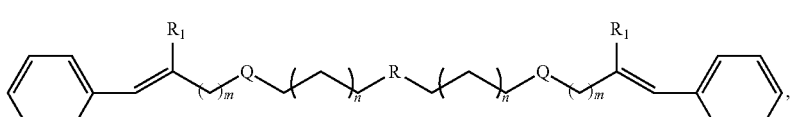

wherein:
each Q is independently selected from the group consisting of —C(O)O—, —C(O)NH—, —OC(O)O—, —O—, —OC(O)— and —NHC(O)—;
R is selected from the group consisting of a substituted or unsubstituted $C_2$ to $C_{100}$ aliphatic or heteroaliphatic, a $C_3$ to $C_8$ cycloaliphatic, a branched aliphatic, a branched hetero aliphatic, a heterocyclic, a heteroaromatic, an aryl, a polyaryl and a silicone containing 2-20 silicon atoms optionally substituted with one or two methyl or phenyl groups;
each $R_1$ is independently selected from the group consisting of H and methyl;
each m is an integer independently having the value of 0 or 1; and
each n is an integer independently having the value of 0 or 1.

18. The method of claim 17, wherein the adhesion is increased by at least about 25% compared with the adhesion of a thermoset obtained from a bismaleimide in the absence of the at least one di-cinnamyl compound.

* * * * *